(12) United States Patent
Sato et al.

(10) Patent No.: US 7,314,877 B2
(45) Date of Patent: Jan. 1, 2008

(54) BENZOFURAN DERIVATIVE

(75) Inventors: Seiichi Sato, Suginami-ku (JP); Tomoyuki Koshi, Shiki (JP); Toshimi Mizoguchi, Iruma (JP); Kyoko Yasuoka, Higashiyamato (JP); Natsuyo Kumai, Fujimi (JP); Junko Totsuka, Nerima-ku (JP); Masahiro Tamura, Machida (JP); Masao Ohkuchi, Tokorozawa (JP)

(73) Assignee: Kowa Co., Ltd., Nagoya-shi (JP)

( * ) Notice: Subject to any disclaimer, the term of this patent is extended or adjusted under 35 U.S.C. 154(b) by 101 days.

(21) Appl. No.: 10/547,779

(22) PCT Filed: Mar. 3, 2004

(86) PCT No.: PCT/JP2004/002633

§ 371 (c)(1),
(2), (4) Date: Sep. 6, 2005

(87) PCT Pub. No.: WO2004/078751

PCT Pub. Date: Sep. 16, 2004

(65) Prior Publication Data

US 2006/0189621 A1    Aug. 24, 2006

Related U.S. Application Data

(60) Provisional application No. 60/452,564, filed on Mar. 7, 2003.

(51) Int. Cl.
*C07D 405/04* (2006.01)
*A61K 31/501* (2006.01)

(52) U.S. Cl. .................. 514/252.01; 544/238
(58) Field of Classification Search ................ 544/238; 514/252.01
See application file for complete search history.

(56) References Cited

U.S. PATENT DOCUMENTS

| | | |
|---|---|---|
| 6,348,468 B1 | 2/2002 | Ohkuchi et al. |
| 6,403,586 B1 | 6/2002 | Ohkuchi et al. |
| 6,664,256 B1 | 12/2003 | Ohkuchi et al. |
| 6,680,316 B1 | 1/2004 | Ohkuchi et al. |
| 6,861,428 B2 | 3/2005 | Kyotani et al. |
| 6,869,954 B2 | 3/2005 | Kyotani et al. |
| 2002/0123496 A1 | 9/2002 | Ohkuchi et al. |
| 2004/0147516 A1 | 7/2004 | Ohkuchi et al. |
| 2005/0065155 A1 | 3/2005 | Ohkuchi et al. |
| 2005/0085480 A1 | 4/2005 | Kyotani et al. |

FOREIGN PATENT DOCUMENTS

| | | |
|---|---|---|
| EP | 0 611 815 | 8/1994 |
| EP | 0 926 137 | 6/1999 |
| JP | 2000-290261 | 10/2000 |
| JP | 2001-151779 | 6/2001 |
| JP | 2001-151780 | 6/2001 |
| JP | 2001-158789 | 6/2001 |
| JP | 2001-511764 | 8/2001 |
| JP | 2005-14808 | 1/2005 |
| WO | 01/22966 | 4/2001 |
| WO | 01/58900 | 8/2001 |
| WO | 01/62715 | 8/2001 |
| WO | 01/62751 | 8/2001 |
| WO | 01/64674 | 9/2001 |

OTHER PUBLICATIONS

R. I. Souhami and J. Moxham ed.; "Textbook of Medicine" (Oct. 2002, Churchill Livingston, UK), see Chapter 4, pp. 79-104.*
Moreland et al. "Etanercept Therapy in Rheumatoid Arthritis: A Randomized, Controlled Trial", Ann Intern Med., vol. 130, pp. 478-486 1999.
Elliott et al. "Randomised double-blind comparison of chimeric monoclonal antibody to tumour necrosis factor alpha (cA2) versus placebo in rheumatoid arthritis", Lancet, vol. 344, pp. 1105-1110 1994.

* cited by examiner

*Primary Examiner*—Kahsay Habte
(74) *Attorney, Agent, or Firm*—Oblon, Spivak, McClelland, Maier & Neustadt, P.C.

(57) ABSTRACT

The present invention is directed to a compound represented by formula (1):

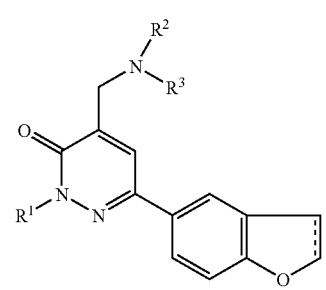

(wherein $R^1$ represents an alkyl group which may have a substituent or an alkenyl group which may have a substituent; and each of $R^2$ and $R^3$ represents a hydrogen atom, an alkyl group, a hydroxyalkyl group, a dihydroxyalkyl group, or an alkynyl group, or $R^2$ and $R^3$ form, together with the nitrogen atom adjacent thereto, a nitrogen-containing saturated heterocyclic group which may have a substituent) and a drug composition containing the compound. The compound exhibits tumor necrosis factor (TNF-α) production inhibitory effect and improved absorption upon oral administration.

9 Claims, 1 Drawing Sheet

BENZOFURAN DERIVATIVE

This application is a 371 of PCT/JP04/02633 filed Mar. 3, 2004 which claims benefit of U.S. provisional application Ser. No. 60/452,564 filed Mar. 7, 2003.

TECHNICAL FIELD

The present invention relates to a benzofuran derivative which exhibits excellent inhibitory effect against production of tumor necrosis factor (TNF-α) and high absorption after oral administration, and thus is useful for preventing or treating allergic diseases, immune diseases, inflammatory diseases, or similar diseases. The present invention also relates to a drug containing the derivative as an active ingredient.

BACKGROUND ART

Tumor necrosis factor (TNF-α) is an inflammatory cytokine produced by cells such as macrophages. It exhibits a variety of physiological activities, and thus is indispensable to protect the living body and maintain homeostasis. Meanwhile, overproduction of tumor necrosis factor (TNF-α) is considered to be responsible for allergic, inflammatory, or autoimmune diseases, such as chronic articular rheumatism, arthritis deformans, asthma, bronchitis, atopic dermatitis, inflammatory visceral disease, ulcerative colitis, Crohn's disease, and acquired immunological deficiency syndrome (AIDS), and thus compounds exhibiting TNF-α production inhibitory effect are expected to function as preventive or therapeutic remedies for these diseases.

Recent studies have reported that anti-TNF-α antibodies and soluble TNF-α receptors exhibit excellent clinical effect (*Lancet* 344 1105 (1994), *Ann. Intern. Med.* 130 478 (1999)), giving more solid grounds for the concept of anti-TNF-α therapy.

These antibodies and receptors are often called biological preparations, and injection is the unavoidable form for administering to a patient. Therefore, there remain needs for a low-molecular-weight compound which exhibits TNF-α production inhibitory effect and can be absorbed when administered via oral route.

Low-molecular-weight compounds heretofore disclosed to have TNF-α production inhibitory effect include oxyindole derivatives (WO 0122966, JP-A-2001-511449), thiazolyl derivatives (WO 0164674), pyrrole derivatives (JP-A-2001-181187, JP-A-2000-514808), piperidylpyrimidine derivatives (JP-A-2001-511764), picolinic acid derivatives (EP 926137), imidazopyridine derivatives (WO 0158900), tetrahydrothieno[2,3-c]pyridine derivatives (JP 13151779, JP 13158789, JP 13151780), and sulfonamide derivatives (WO 01/62751, WO 01/62715). However, none of these publications disclose specific information regarding absorption following oral administration.

Another compound; i.e., dihydropyridazinone derivative, has also been disclosed as having TNF-α production inhibitory effect (JP-A-2000-290261), but it greatly differs from the compounds of the present invention in terms of chemical structure.

DISCLOSURE OF THE INVENTION

The present inventors have found that there can be obtained, by introducing a pyridazinyl group into a benzofuran skeleton at the 5-position thereof, a compound which exhibits good absorption after oral administration and excellent TNF-α production inhibitory effect and thus is useful as a drug for preventing or treating, for example, allergic diseases, immune diseases, or inflammatory diseases. The present invention has been accomplished based on such a finding.

Accordingly, the present invention provides a benzofuran derivative represented by formula (1):

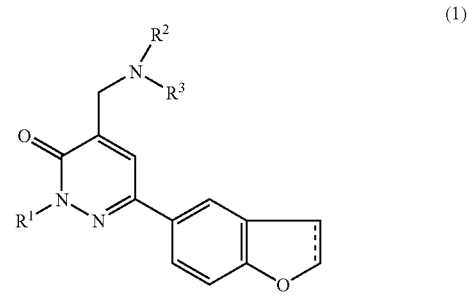

(wherein $R^1$ represents an alkyl group which may have a substituent or an alkenyl group which may have a substituent;

each of $R^2$ and $R^3$ represents a hydrogen atom, an alkyl group, a hydroxyalkyl group, a dihydroxyalkyl group, or an alkynyl group, or $R^2$ and $R^3$ form, together with the nitrogen atom adjacent thereto, a nitrogen-containing saturated heterocyclic group which may have a substituent; and the broken line denotes the possible presence of a double bond)

or a salt thereof.

The present invention also provides a drug containing, as an active ingredient, a benzofuran derivative (1) or a salt thereof.

The present invention also provides a drug composition containing a benzofuran derivative (1) or a salt thereof and a pharmacologically acceptable carrier therefor.

The present invention also provides a method for treating pathological conditions caused by excessive production of tumor necrosis factor (TNF-α), characterized by administering a benzofuran derivative (1) or a salt thereof.

The present invention also provides use of a benzofuran derivative (1) or a salt thereof in manufacture of a drug.

The compound (1) of the present invention exhibits excellent tumor necrosis factor (TNF-α) production inhibitory effect and enhanced absorption after oral administration, and therefore is useful for preventing or treating allergic diseases, immune diseases, inflammatory diseases, or similar pathological conditions.

BEST MODE FOR CARRYING OUT THE INVENTION

Figure 1:
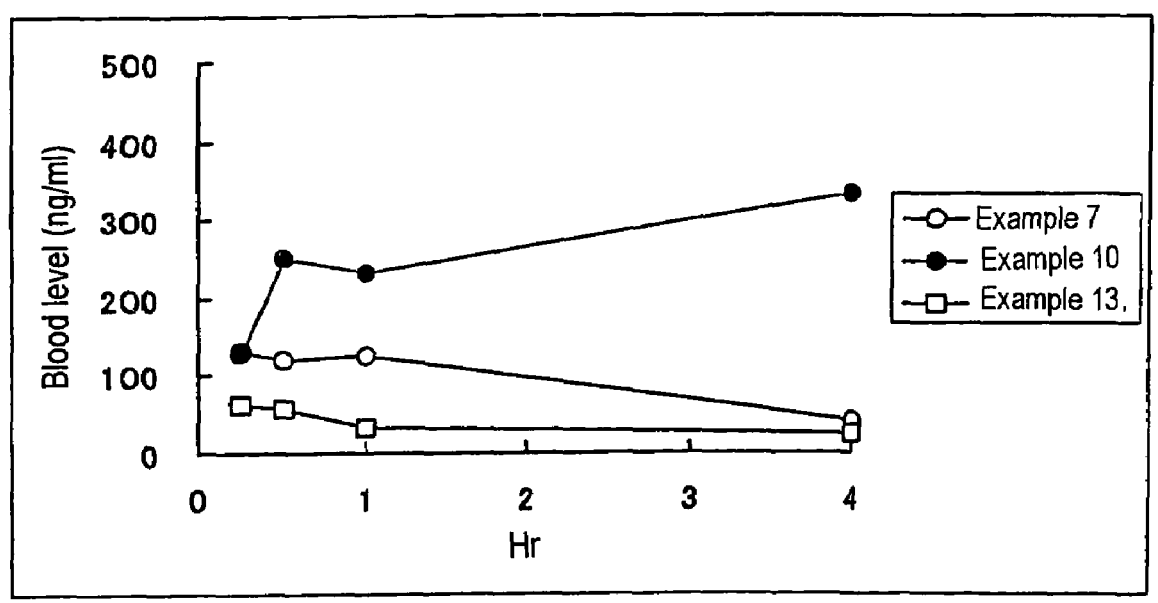
FIG. 1 shows absorption after oral administration of the compounds according to the present invention (Examples 7, 10, and 13).

In formula (1), when alkyl, hydroxyalkyl, or dihydroxyalkyl groups are referred to, either the alkyl group or the alkyl moiety of the hydroxyalkyl or dihydroxyalkyl group is C1-C12 alkyl, more preferably C1-C7 alkyl. The alkyl group/moiety may be linear, branched, or cyclic, or may have a ring structure. Examples of the alkyl group/moiety include methyl, ethyl, n-propyl, isopropyl, n-butyl, isobutyl, cyclopropyl, cyclobutyl, cyclopentyl, cyclohexyl, cyclopropylmethyl, cyclopropylethyl, cyclobutylmethyl, cyclopentylmethyl, and cyclohexylmethyl.

In formula (1), the alkyl group represented by $R^1$ is C1-C12 alkyl, preferably C1-C7 alkyl, more preferably C1-C5 alkyl. The alkyl group may be linear, branched, or cyclic, or may have a ring structure. Examples of the alkyl group represented by $R^1$ include methyl, ethyl, propyl, isobutyl, cyclobutyl, cyclopentyl, cyclohexyl, cyclopropylmethyl, cyclopropylethyl, cyclobutylmethyl, cyclopentylmethyl, and cyclohexylmethyl, with methyl, ethyl, isobutyl, cyclopropylmethyl, or cyclopentylmethyl being preferred.

The alkenyl group represented by $R^1$ is preferably C2-C12 alkenyl, more preferably C2-C7 alkenyl, particularly preferably C2-C5 alkenyl. The alkenyl group may be linear or branched, and examples of the alkenyl group include vinyl, propenyl, butenyl, and pentenyl.

Examples of the substituent which may be possessed by the alkyl or alkenyl group represented by $R^1$ include an aryl group which may have a substituent and a heteroaryl group which may have a substituent. The aryl group may be a C6-C14 aryl group, and examples of the aryl group include phenyl and naphthyl, wherein phenyl is preferred. The heteroaryl group may be a heteroaryl group which has a 5-membered or 6-membered ring containig one to three nitrogen atoms, and examples of the heteroaryl group include pyrrolyl, imidazolyl, pyrazolyl, pyridyl, pyrimidinyl, pyrazinyl, and pyridazinyl, with pyridyl being preferred.

The aryl or heteroaryl group may have one to three substituents. Examples of the substituents include a halogen atom, an alkyl group, and an alkoxy group. Examples of the halogen atom include fluorine, chlorine, bromine, and iodine, wherein fluorine and chlorine are preferred. The alkyl group is preferably C1-C12 alkyl, more preferably C1-C7 alkyl. The alkoxy group is preferably C1-C12 alkoxy, more preferably C1-C7 alkoxy.

Either the alkyl group represented by $R^2$ or $R^3$ or the alkyl moiety of the hydroxyalkyl or dihydroxyalkyl group represented by $R^2$ or $R^3$ is preferably C1-C12 alkyl, more preferably C1-C7 alkyl. The alkyl group/moiety is preferably linear or branched, and examples of the alkyl group/moiety include methyl, ethyl, n-propyl, isopropyl, n-butyl, isobutyl, hydroxyethyl, hydroxypropyl, hydroxybutyl, dihydroxypropyl, and dihydroxybutyl.

Examples of the alkynyl group represented by $R^2$ or $R^3$ include C3-C12 alkynyl, particularly C3-C7 alkynyl, such as propargyl (2-propynyl).

Examples of the nitrogen-containing saturated heterocyclic group which is formed from $R^2$, $R^3$, and the nitrogen atom adjacent thereto include 5-membered, 6-membered, and 7-membered saturated heterocyclic groups. Specific examples include pyrrolidinyl, piperidino, piperazinyl, homopiperazinyl, and morpholino, wherein piperazinyl, piperidino, and morpholino are preferred.

Examples of the substituent which may be possessed by the heterocyclic group include a halogen atom, an alkyl group, alkoxycarbonyl group, and an aralkyl group. Examples of the halogen atom include fluorine, chlorine, bromine, and iodine. Examples of the alkyl group include C1-C12 alkyl groups, with C1-C7 alkyl groups being preferred. Examples of the alkoxycarbonyl group include C1-C12 alkyloxycarbonyl groups, with C1-C7 alkoxycarbonyl groups being preferred. The aralkyl group is preferably phenyl-C1-C7 alkyl groups, with a benzyl group being particularly preferred.

In formula (1), the broken line denotes the possible presence of a double bond. However, the absence of double bond is preferred.

In formula (1), $R^1$ is particularly preferably isobutyl, cyclopropylmethyl, cyclopentylmethyl, cinnamyl, halogenocinnamyl, benzyl, halogenobenzyl, dihalogenobenzyl, or (halogenophenyl)propyl. Each of $R^2$ and $R^3$ is preferably a hydrogen atom, a C1-C7 alkyl group, a C1-C7 hydroxyalkyl group, or a propargyl group. The heterocyclic group formed by $R^2$ and $R^3$ is preferably a piperazinyl group, a piperidino group, a pyrrolidino group, or a morpholino group, wherein each of the four groups may optionally be substituted by a C1-C7 alkyl group or a benzyl group.

The salt form of the compound (1) of the present invention is preferably an acid-addition salt. Examples of the acid-addition salt include inorganic acid salts such as hydrochloride, sulfate, nitrate, and phosphate, and organic acid salts such as methanesulfonate, maleate, fumarate, citrate, and oxalate.

The compounds of the present invention may be in the form of solvates or keto-enol tautomers. The present invention also encompasses such solvates and tautomers. No particular limitation is imposed on the type of the solvate, so long as the solvate does not adversely affect tumor necrosis factor (TNF-α) production inhibitory effect, among other effects, and the solvate may be formed from a solvent employed in the production or other steps, such as water or alcohol. The solvate is preferably a hydrate.

The compound (1) of the present invention can be produced through, for example, the following production process:

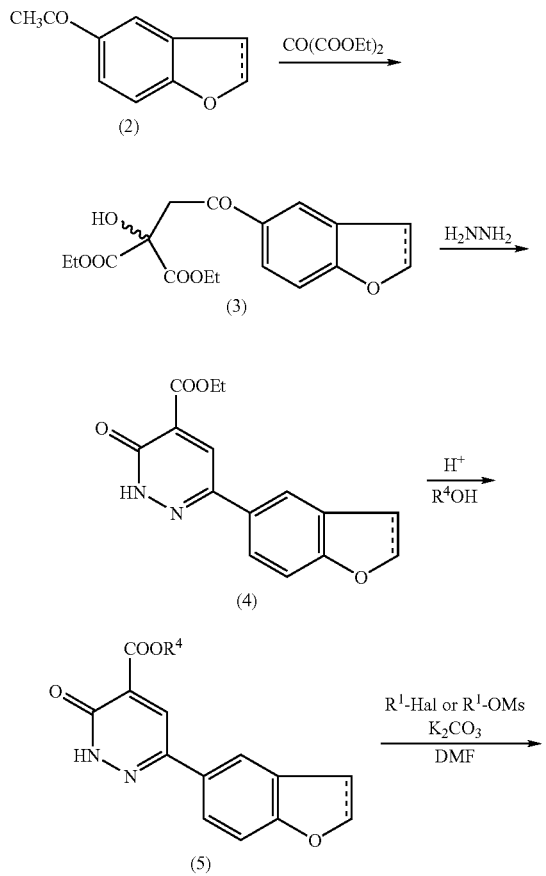

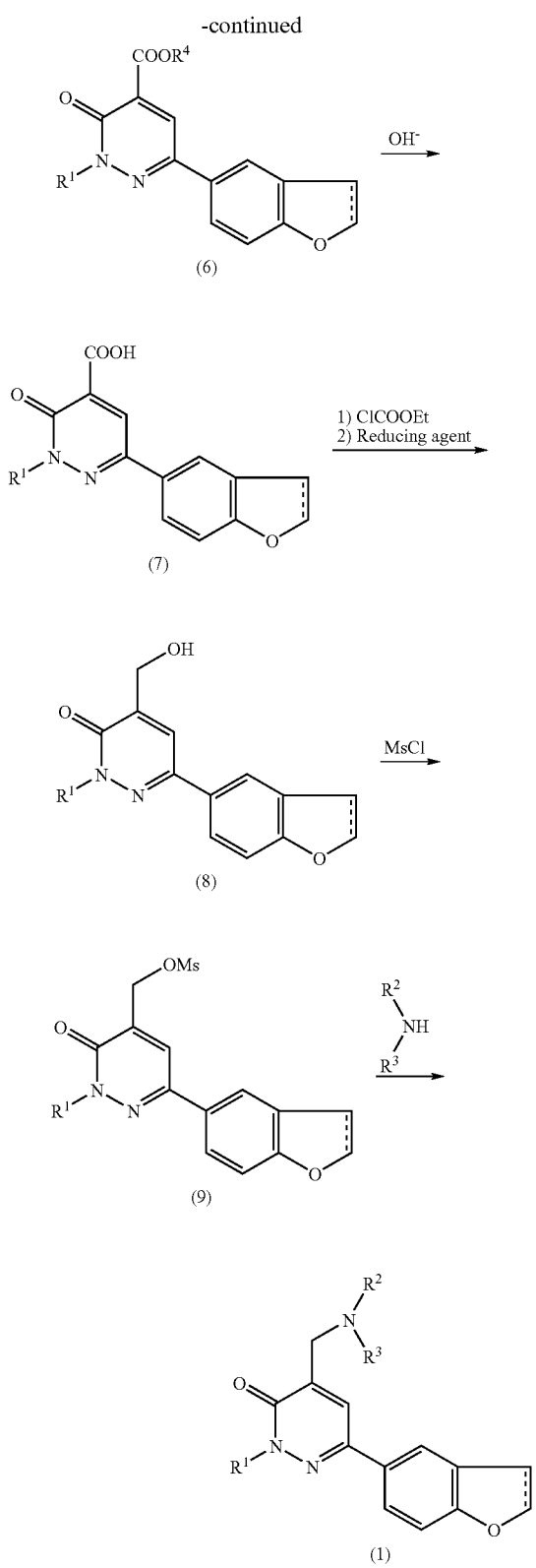

(wherein R⁴ represents an alkyl group; Hal represents a halogen atom; Ms represents a methanesulfonyl group; and each of R¹, R², and R³ has the same meaning as described above)

The reaction steps of the production process will next be described.

Firstly, steps involved in production of compound (5) from acetophenone (2) will be described. Acetophenone (2) and diethyl ketomalonate are heated under stirring to thereby produce compound (3). The compound (3) is reacted with hydrazine so as to form a ring, followed by treatment with an alkali (e.g., sodium hydroxide), to thereby give compound (4). The compound (4) is reacted with an alcohol (e.g., methanol), to thereby give compound (5).

The thus-produced compound (5) is reacted with R¹-Hal or R¹-OMs in the presence of an alkali (e.g., potassium carbonate), to thereby produce compound (6). The compound (6) is hydrolyzed to thereby give compound (7), which is subsequently reacted with chloroethyl carbonate, to thereby give an acid anhydride. The acid anhydride is reduced by use of a reducing agent (e.g., sodium borohydride), to thereby give compound (8). The compound (8) is reacted with methanesulfonyl chloride in the presence of a base (e.g., triethylamine), to thereby produce compound (9), serving as a key intermediate compound of the production process.

The target compound (1) can be produced by reacting the compound (9) with an amine (R²(R³)NH) of interest. The reaction is preferably performed in a polar solvent (e.g., acetonitrile) and in the presence or absence of an alkali (e.g., potassium carbonate). When R² or R³ of the amine has an amino group, the amino group of the starting amine may be protected in advance with an appropriate protecting group (e.g., an alkoxycarbonyl group), and the protecting group is removed after completion of reaction.

When the compound (1) in which each of R² and R³ represents hydrogen is produced, there may be employed a process in which the compound (9) is reacted with potassium phthalimide and then with hydrazine or a similar compound.

The salt of the compound (1) of the present invention is produced through reaction of the compound with an organic acid or an inorganic acid through a routine method.

The separation/purification of the compound (1) of the present invention can be performed through a purification method generally employed in the field of organic synthesis chemistry, such as filtration, extraction, washing, drying, concentration, recrystallization, or chromatography. The intermediates of the production process can be used in the subsequent reaction step without performing further purification. The compound (1) of the present invention may be produced in the form of solvate of a solvent such as reaction solvent or recrystallization solvent, particularly in the form of hydrate.

As shown in the Experimental Examples described below, the compound (1) of the present invention exhibits excellent TNF-α production inhibitory effect and exhibits improved absorption after oral administration. Therefore, the compound (1) is useful as a drug for preventing or treating pathological conditions of mammals, including humans, caused by excessive production of TNF-α, such as allergic diseases, inflammatory diseases, and autoimmune diseases. Specific examples of the pathological conditions caused by excessive production of TNF-α include chronic articular rheumatism, arthritis deformans, asthma, bronchitis, atopic dermatitis, inflammatory visceral diseases, ulcerative colitis, Crohn's disease, and acquired immunological deficiency syndrome (AIDS).

The drug composition of the present invention contains the compound (1) as an active ingredient. The active ingredient, compound (1), can be processed, into a drug preparation, singly or in combination with one or more pharmacologically acceptable carriers (e.g., solubilizer, excipient, binder, and diluent). Examples of the physical form of the drug preparation include tablets, capsules, granules, powders, injections, and suppositories. The drug preparation can be produced through a known method. For example, a drug preparation for oral administration can be produced through processing the compound (1) with one or more suitably selected carriers such as a solubilizer (e.g., tragacanth gum, acacia, a sucrose ester, lecithin, olive oil, soybean oil, or PEG400), an excipient (e.g., starch, mannitol, or lactose), a binder (e.g., sodium carboxymethylcellulose or hydroxypropylcellulose), a disintegrant (e.g., crystalline cellulose or calcium carboxymethylcellulose), a lubricant (e.g., talc or magnesium stearate), and a flowability-improving agent (e.g., light anhydrous silicic acid). The drug composition of the present invention is orally or parenterally administered.

The dose of the drug composition of the present invention varies depending on, among others, the body weight, age, sex, or pathological condition of the patient. The daily dose of compound (1) for an adult is typically 0.01 to 1,000 mg, preferably 0.1 to 100 mg. The compound (1) is preferably administered once a day or two or three times a day in a divided manner.

EXAMPLES

The present invention will next be described in more detail by way of examples, which should not be construed as limiting the invention thereto.

Example 1

Production of 2-cyclopropylmethyl-6-(2,3-dihydro-1-benzofuran-5-yl)-4-(4-methyl-1-piperazinyl)methyl-2H-pyridazin-3-one 1) Production of 4-carboxy-6-(2,3-dihydro-1-benzofuran-5-yl)-2H-pyridazin-3-one 5-Acetylcoumarane [Brown H. C., Inukai T., J. Am. Chem. Soc., 83 4825 (1961)] (5.0 g, 30.8 mmol) and diethyl ketomalonate (5.9 g, 33.9 mmol) were mixed together, and the mixture was stirred for 39 hours at 120° C. The reaction mixture was dissolved in isopropanol (100 mL), and hydrazine monohydrate (3.38 g, 67.5 mmol) was added to the resultant mixture, followed by stirring for six hours at 100° C. A 2-mol/L aqueous sodium hydroxide solution (7 mL) was added thereto, and the resultant mixture was stirred for four hours at 100° C. The reaction mixture was cooled on ice and acidified with concentrated hydrochloric acid. The formed precipitates were collected through filtration and thoroughly washed with water, followed by drying, to thereby yield 5.9 g of the title compound as a yellow powder (74.1%).

2) Production of 6-(2,3-dihydro-1-benzofuran-5-yl)-4-methoxycarbonyl-2H-pyridazin-3-one 4-Carboxy-6-(2,3-dihydro-1-benzofuran-5-yl)-2H-pyridazin-3-one (5.9 g, 22.8 mmol) was suspended in methanol (100 mL), and thionyl chloride (3 g, 25.1 mmol) was added dropwise to the suspension under cooling with ice, followed by stirring for three hours at 80° C. The temperature of the reaction mixture was reduced to room temperature, and the solvent was removed under reduced pressure. Water was added to the residue under cooling on ice, and the formed precipitates were collected through filtration and washed with water, followed by drying, to thereby yield 4.90 g of the title compound as pale yellow micro-needles (78.8%).

m.p.: 192-200° C. $^1$H NMR (400 MHz, CDCl$_3$)δ: 3.28 (2H, t, J=8.3 Hz), 3.99 (3H, s), 4.66 (2H, t, J=8.3 Hz), 6.87 (1H, d, J=8.3 Hz), 7.56 (1H, d, J=8.3 Hz), 7.68 (1H, s). 8.31 (1H, s).

3) Production of 4-carboxy-2-cyclopropylmethyl-6-(2,3-dihydro-1-benzofuran-5-yl)-2H-pyridazin-3-one 6-(2,3-Dihydro-1-benzofuran-5-yl)-4-methoxycarbonyl-2H-pyridazin-3-one (2.0 g, 7.35 mmol) was dissolved in N,N-dimethylformamide (17 mL), and potassium carbonate (2.0 g, 14.7 mmol) and bromomethylcyclopropane (1.2 g, 8.8 mmol) were added to the resultant solution, followed by stirring for two hours at 80° C. The temperature of the reaction mixture was reduced to room temperature, and saturated aqueous sodium hydrogencarbonate solution was added thereto, followed by extraction with ethyl acetate. The organic layer was washed with saturated brine and dried over sodium sulfate anhydrate, and the solvent was removed through distillation, to thereby yield 2.66 g of a crude product. The crude product was suspended in methanol (20 mL), and a 2-mol/L aqueous sodium hydroxide solution (20 mL) was added thereto, followed by stirring for one hour at 60° C. After the temperature of the reaction mixture had been reduced to room temperature, water was added thereto, and the mixture was acidified with concentrated hydrochloric acid, followed by extraction with ethyl acetate. The organic layer was washed with saturated brine and dried over sodium sulfate anhydrate. The solvent was removed under reduced pressure, and the residue was recrystallized from chloroform-hexane, to thereby yield 1.88 g of the title compound as a yellow powder (81.7%).

m.p.: 160-165° C. $^1$H NMR (400 MHz, CDCl$_3$)δ: 0.50-0.55 (2H, m), 0.60-0.66 (2H, m), 1.46 (1H, m), 3.30 (2H, t, J=8.8 Hz), 4.22 (2H, t, J=7.3 Hz), 4.67 (2H, t, J=8.8 Hz), 6.89 (1H, d, J=8.5 Hz), 7.65 (1H, dd, J=8.5, 2.0 Hz), 7.72 (1H, s). 8.62 (1H, s).

4) Production of 2-cyclopropylmethyl-6-(2,3-dihydro-1-benzofuran-5-yl)-4-hydroxymethyl-2H-pyridazin-3-one To a solution of 4-carboxy-2-cyclopropylmethyl-6-(2,3-dihydro-1-benzofuran-5-yl)-2H-pyridazin-3-one (1.8 g, 5.76 mmol) in THF (25 mL), triethylamine (641 mg, 6.34 mmol) was added, and a solution of chloroethyl carbonate (688 mg, 6.34 mmol) in THF (1 mL) was added dropwise to the resultant mixture under cooling with ice, followed by stirring for 30 minutes. The formed triethylamine hydrochloride was removed through filtration, and a solution of sodium borohydride (327 mg, 8.64 mmol) in water (2 mL) was added to the filtrate under cooling with ice, followed by stirring for 15 minutes at room temperature. Aqueous hydrochloric acid (2 mol/L) was added to the reaction mixture, and the resultant mixture was extracted with ethyl acetate. The organic layer was washed with saturated brine and dried over sodium sulfate anhydrate. The solvent was removed under reduced pressure, and the residue was subjected to a separation/purification step through silica gel column chromatography [silica gel 60 g, chloroform/methanol (100/1)], to thereby yield 566 mg of the title compound as pale yellow powder (32.9%).

m.p.: 115-117° C. $^1$H NMR (400 MHz, CDCl$_3$)δ: 0.46-0.51 (2H, m), 0.54-0.60 (2H, m), 1.43 (1H, m), 3.28 (2H, t, J=8.8 Hz), 4.10 (2H, d, J=7.1 Hz), 4.64 (2H, d, J=8.8 Hz), 4.71 (2H, d, J=0.73 Hz), 6.85 (1H, d, J=8.5 Hz), 7.55 (1H, dd, J=8.5, 2.0 Hz), 7.63 (1H, s), 7.68 (1H, s).

5) Production of 2-cyclopropylmethyl-6-(2,3-dihydro-1-benzofuran-5-yl)-4-methanesulfonyloxymethyl-2H-pyridazin-3-one 2-Cyclopropylmethyl-6-(2,3-dihydro-1-benzofuran-5-yl)-4-hydroxymethyl-2H-pyridazin-3-one (540 mg, 1.81 mmol) was dissolved in methylene chloride (12 mL), and triethylamine (238 mg, 2.35 mmol) and methanesulfonyl chloride (249 mg, 2.17 mmol) were added to the solution under cooling with ice, followed by stirring for one hour. A saturated aqueous sodium hydrogencarbonate solution was added to the reaction mixture, and the resultant mixture was extracted with ethyl acetate. The organic layer was washed with saturated brine and dried over sodium sulfate anhydrate. The solvent was removed under reduced pressure, and the residue was recrystallized from chloroform-hexane, to thereby yield 607 mg of the title compound as a pale yellow crystalline powder (89.1%).

m.p.: 108-111° C. $^1$H NMR (400 MHz, CDCl$_3$)δ: 0.45-0.50 (2H, m), 0.53-0.60 (2H, m), 1.42 (1H, m), 3.17 (3H, s), 3.29 (2H, t, J=8.8 Hz), 4.10 (2H, d, J=7.3 Hz), 4.65 (2H, t, J=8.8 Hz), 5.28 (2H, d, J=0.97 Hz), 6.86 (1H, d, J=8.3 Hz), 7.56 (1H, dd, J=8.3, 2.0 Hz), 7.67 (1H, s), 7.75 (1H, s).

6) Production of 2-cyclopropylmethyl-6-(2,3-dihydro-1-benzofuran-5-yl)-4-(4-methyl-1-piperazinyl)methyl-2H-pyridazin-3-one 2-Cyclopropylmethyl-6-(2,3-dihydro-1-benzofuran-5-yl)-4-methanesulfonyloxymethyl-2H-pyridazin-3-one (100 mg, 0.27 mmol) was dissolved in acetonitrile (1.5 mL), and potassium carbonate (55 mg, 040 mmol) and 1-methylpiperazine (32 mg, 0.32 mmol) were added to the solution, followed by stirring for three hours at 80° C. The temperature of the reaction mixture was reduced to room temperature, and water was added thereto. The resultant mixture was extracted with chloroform, and the organic layer was dried over sodium sulfate anhydrate. The solvent was removed under reduced pressure, and the residue was subjected to separation/purification through separative thin-layer silica gel chromatography [chloroform/methanol (10/1)], followed by recrystallization from chloroform-hexane, to thereby yield 54 mg of the title compound as pale yellow needle-like crystal (53.5%).

m.p.: 128-130° C. $^1$H NMR (400 MHz, CDCl$_3$)δ: 0.45-0.57 (4H, m), 1.42 (1H, m), 2.43 (3H, s), 2.60-3.00 (8H, m), 3.29 (2H, t, J=8.8 Hz), 3.61 (2H, s), 4.09 (2H, d, J=7.2 Hz), 4.64 (2H, t, J=8.8 Hz), 6.82 (1H, d, J=8.3 Hz), 7.55 (1H, d, J=8.3 Hz), 7.69 (1H, s), 7.71 (1H, s). IR (KBr) cm$^{-1}$: 1651, 1608, 1501, 1242, 1168, 808. Mass m/z: 380(M$^+$).

Example 2

Production of 4-N,N-bis(2-hydroxyethyl)aminomethyl-2-cyclopropylmethyl-6-(2,3-dihydro-1-benzofuran-5-yl)-2H-pyridazin-3-one The general procedure of Example 1 (6) was carried out by use of 2-cyclopropylmethyl-6-(2,3-dihydro-1-benzofuran-5-yl)-4-methanesulfonyloxymethyl-2H-pyridazin-3-one and diethanolamine, to thereby yield the title compound as a yellow oil (yield: 74.5%).

$^1$H NMR (400 MHz, CDCl$_3$)δ: 0.40-0.65 (4H, m), 1.42 (1H, m), 2.70-3.05 (4H, m), 3.28 (2H, t, J=8.8 Hz), 3.50-4.00 (6H, m), 4.11 (2H, d, J=8.5 Hz), 4.64 (2H, t, J=8.8 Hz), 6.85 (1H, d, J=8.5 Hz), 7.58 (1H, d, J=8.5 Hz), 7.71 (1H, s), 7.80 (1H, s). IR (Neat) cm$^1$: 3392, 1645, 1602, 1516, 1238, 1047. Mass m/z: 354(M$^+$-CH$_2$OH).

Example 3

Production of 2-cyclopropylmethyl-6-(2,3-dihydro-1-benzofuran-5-yl)-4-dimethylaminomethyl-2H-pyridazin-3-one To 2-cyclopropylmethyl-6-(2,3-dihydro-1-benzofuran-5-yl)-4-methanesulfonyloxymethyl-2H-pyridazin-3-one (120 mg, 0.32 mmol), a 40% aqueous dimethylamine solution (2 mL) was added, and the mixture was stirred for two hours at 80° C. The temperature of the reaction mixture was reduced to room temperature, and water was added to the reaction mixture. The resultant mixture was extracted with chloroform, and the organic layer was dried over sodium sulfate anhydrate. The solvent was removed under reduced pressure, and the residue was recrystallized from chloroform-hexane, to thereby yield 53 mg (51.1%) of the title compound as a yellow powder.

m.p.: 109-110° C. $^1$H NMR (400 MHz, CDCl$_3$)δ: 0.45-0.56 (4H, m), 1.43 (1H, m), 2.44 (3H, s), 3.28 (2H, t, J=8.8 Hz), 3.62 (2H, s), 4.10 (2H, d, J=7.3 Hz), 4.63 (2H, t, J=8.8 Hz), 6.85 (1H, d, J=8.3 Hz), 7.62 (1H, d, J=8.3 Hz), 7.72 (1H, s), 7.92 (1H, m). IR (KBr) cm$^{-1}$: 1651, 1606, 1499, 1243, 1102, 820. Mass m/z: 325(M$^+$).

Example 4

Production of 2-cyclopropylmethyl-6-(2,3-dihydro-1-benzofuran-5-yl)-4-(1-piperazinyl)methyl-2H-pyridazin-3-one 1) Production of 4-(4-tert-butoxycarbonyl-1-piperazinyl)methyl-2-cyclopropylmethyl-6-(2,3-dihydro-1-benzofuran-5-yl)-2H-pyridazin-3-one The general procedure of Example 1 (6) was repeated by use of 2-cyclopropylmethyl-6-(2,3-dihydro-1-benzofuran-5-yl)-4-methanesulfonyloxymethyl-2H-pyridazin-3-one and tert-butyl-1-piperazine carboxylate, to thereby yield the title compound as a yellow oil (yield: 97.6%).

$^1$H NMR (400 MHz, CDCl$_3$)δ: 0.45-0.50 (2H, m), 0.51-0.58 (2H, m), 1.42 (1H, m), 1.47 (9H, s), 2.45-2.60 (4H, m), 3.29 (2H, t, J=8.8 Hz), 3.45-3.55 (4H, m), 3.58 (2H, brs), 4.10 (2H, d, J=7.1 Hz), 4.64 (2H, t, J=8.8 Hz), 6.86 (1H, d, J=8.3 Hz), 7.55 (1H, m), 7.69 (1H, s), 7.75 (1H, m).

2) Production of 2-cyclopropylmethyl-6-(2,3-dihydro-1-benzofuran-5-yl)-4-(1-piperazinyl)methyl-2H-pyridazin-3-one 4-(4-tert-Butoxycarbonyl-1-piperazinyl)methyl-2-cyclopropylmethyl-6-(2,3-dihydro-1-benzofuran-5-yl)-2H-pyridazin-3-one (121 mg, 0.26 mmol) was dissolved in trifluoroacetic acid (1.1 mL) under cooling with ice-water, and the solution was stirred for 15 minutes at the same temperature. Water (10 mL) was added to the reaction mixture, and the resultant mixture was made alkaline with potassium carbonate, followed by extraction with chloroform. The organic layer was washed with saturated brine (20 mL) and dried over sodium sulfate anhydrate, and the solvent was removed under reduced pressure, to thereby yield 83 mg (87.4%) of the title compound as a yellow oil.

$^1$H NMR (400 MHz, CDCl$_3$)δ: 0.44-0.58 (4H, m), 1.43 (1H, m), 2.58-2.70 (5H, m), 2.99-3.10 (4H, m), 3.29 (2H, t, J=8.5 Hz), 3.57 (2H, s), 4.09 (2H, d, J=7.3 Hz), 4.64 (2H, t, J=8.5 Hz), 6.86 (1H, d, J=8.3 Hz), 7.56 (1H, d, J=8.3 Hz), 7.68 (1H, s), 7.74 (1H, m). IR (Neat) cm$^{-1}$: 1652, 1607, 1497, 1238, 1102, 821. Mass m/z: 366(M$^+$).

Example 5

Production of 4-aminomethyl-2-cyclopropylmethyl-6-(2,3-dihydro-1-benzofuran-5-yl)-2H-pyridazin-3-one 2-Cyclopropylmethyl-6-(2,3-dihydro-1-benzofuran-5-yl)-4-methanesulfonyloxymethyl-2H-pyridazin-3-one (140 mg, 0.37 mmol) and potassium phthalimide (83 mg, 0.56 mmol) were added to N,N-dimethylformamide (4 mL), and the mixture was stirred for two hours at 80° C. Water was added to the reaction mixture, and the resultant mixture was extracted with chloroform, followed by washing with saturated brine (20 mL) and drying over sodium sulfate anhydrate. The solvent was removed under reduced pressure, to thereby yield a crude product. The crude product was dissolved in methanol (4.2 mL), and hydrazine monohydrate (91 mg, 1.85 mmol) was added to the solution, followed by reflux for two hours. Methanol was removed under reduced pressure, and chloroform was added to the residue, followed by washing sequentially with water and saturated brine and drying over sodium sulfate anhydrate. The solvent was removed under reduced pressure, and the residue was subjected to separation/purification through separative thin-layer silica gel chromatography (eluent: chloroform/10% w/v ammonia-methanol (20/1)), to thereby yield 91 mg of the title compound (82.3%) as a yellow oil.

$^1$H NMR (400 MHz, CDCl$_3$)δ: 0.44-0.60 (4H, m), 1.42 (1H, m), 3.27 (2H, t, J=8.8 Hz), 3.92 (2H, s), 4.09 (2H, d, J=7.1 Hz), 4.63 (2H, t, J=8.8 Hz), 6.84 (1H, d, J=8.3 Hz), 7.56 (1H, dd, J=8.3, 1.2 Hz), 7.69 (1H, d, J=1.2 Hz), 8.02 (1H, s). IR (Neat) cm$^{-1}$: 1648, 1605, 1498, 1238, 1105, 754. Mass m/z: 297(M$^+$).

Example 6

Production of 2-(4-fluorobenzyl)-6-(2,3-dihydro-1-benzofuran-5-yl)-4-(4-methyl-1-piperazinyl)methyl-2H-pyridazin-3-one 1) Production of 4-carboxy-2-(4-fluorobenzyl)-6-(2,3-dihydro-1-benzofuran-5-yl)-2H-pyridazin-3-one The general procedure of Example 1 (3) was carried out by use of 6-(2,3-dihydro-1-benzofuran-5-yl)-4-methoxycarbonyl-2H-pyridazin-3-one and 4-fluorobenzyl chloride, to thereby yield the title compound as a yellow powder (yield: 54.7%).

m.p.: 215-218° C. $^1$H NMR (400 MHz, CDCl$_3$)δ: 3.30 (2H, t, J=8.8 Hz), 4.68 (2H, t, J=8.8 Hz), 5.46 (2H, s), 6.87 (1H, d, J=8.5 Hz), 7.04-7.08 (2H, m), 7.50-7.54 (2H, m), 7.63 (1H, dd, J=8.5, 2.0 Hz), 7.70 (1H, s), 8.60 (1H, s), 14.06 (1H, s).

2) Production of 2-(4-fluorobenzyl)-6-(2,3-dihydro-1-benzofuran-5-yl)-4-hydroxymethyl-2H-pyridazin-3-one The general procedure of Example 1 (4) was carried out by use of 4-carboxy-2-(4-fluorobenzyl)-6-(2,3-dihydro-1-benzofuran-5-yl)-2H-pyridazin-3-one, to thereby yield the title compound as a yellow oil (yield: 43.4%).

$^1$H NMR (400 MHz, CDCl$_3$)δ: 3.28 (2H, t, J=8.8 Hz), 4.64 (2H, t, J=8.8 Hz), 4.69 (2H, d, J=1.2 Hz), 5.35 (2H, s), 6.85 (1H, d, J=8.5 Hz), 6.98-7.04 (2H, m), 7.46-7.50 (2H, m), 7.55 (1H, dd, J=8.5, 2.0 Hz), 7.64 (1H, s), 7.67 (1H, brs).

3) Production of 2-(4-fluorobenzyl)-6-(2,3-dihydro-1-benzofuran-5-yl)-4-methanesulfonyloxymethyl-2H-pyridazin-3-one The general procedure of Example 1 (5) was carried out by use of 2-(4-fluorobenzyl)-6-(2,3-dihydro-1-benzofuran-5-yl)-4-hydroxymethyl-2H-pyridazin-3-one, to thereby yield the title compound as a yellow oil (yield: 78.6%).

$^1$H NMR (400 MHz, CDCl$_3$)δ: 3.14 (3H, s), 3.29 (2H, t, J=8.8 Hz), 4.65 (2H, t, J=8.8 Hz), 5.27 (2H, d, J=1.5 Hz), 5.35 (2H, s), 6.86 (1H, d, J=8.5 Hz), 6.98-7.05 (2H, m), 7.45-7.50 (2H, m), 7.55 (1H, dd, J=8.5, 2.0 Hz), 7.65 (1H, brs), 7.75 (1H, brs).

4) Production of 2-(4-fluorobenzyl)-6-(2,3-dihydro-1-benzofuran-5-yl)-4-(4-methyl-1-piperazinyl)methyl-2H-pyridazin-3-one The general procedure of Example 1 (6) was repeated by use of 2-(4-fluorobenzyl)-6-(2,3-dihydro-1-benzofuran-5-yl)-4-methanesulfonyloxymethyl-2H-pyridazin-3-one, to thereby yield the title compound as a pale yellow powder (yield: 54.8%).

m.p.: 179-180° C. $^1$H NMR (400 MHz, CDCl$_3$)δ: 2.43 (3H, s), 2.64-2.74 (8H, m), 3.29 (2H, t, J=8.5 Hz), 3.58 (2H, s), 4.65 (2H, t, J=8.5 Hz), 5.34 (2H, s), 6.86 (1H, d, J=8.5 Hz), 6.98-7.04 (2H, m), 7.46-7.51 (2H, m), 7.54 (1H, dd, J=8.5, 2.0 Hz), 7.67 (1H, d, J=2.0 Hz), 7.70 (1H, s). IR (KBr) cm$^{-1}$: 1653, 1609, 1501, 1240, 1119, 819. Mass m/z: 434(M$^+$).

Example 7

Production of 2-(4-fluorobenzyl)-6-(2,3-dihydro-1-benzofuran-5-yl)-4-(4-methyl-1-piperazinyl)methyl-2H-pyridazin-3-one dihydrochloride To a solution of 2-(4-fluorobenzyl)-6-(2,3-dihydro-1-benzofuran-5-yl)-4-(4-methyl-1-piperazinyl)methyl-2H-pyridazin-3-one (109 mg, 0.25 mmol) in methanol (1 mL), a 4-mol/L solution (0.15 mL) of hydrochloric acid in ethyl acetate was added dropwise under stirring at room temperature. The solvent was removed under reduced pressure, and the residue was recrystallized from methanol-ether, to thereby yield 112 mg (88.0%) of the title compound as pale yellow needle-like crystal.

m.p.: 201-204° C. (dec.) $^1$H NMR (400 MHz, CDCl$_3$)δ: 2.79 (3H, s), 2.99 (4H, brs), 3.13 (2H, brs), 3.30 (2H, t, J=8.8 Hz), 3.45 (2H, brs), 3.67 (2H, s), 4.65 (2H, t, J=8.8 Hz), 5.34 (2H, s), 6.86 (1H, d, J=8.3 Hz), 7.01 (2H, dd, J=8.8, 8.8 Hz), 7.49 (2H, dd, J=8.8, 5.4 Hz), 7.60 (1H, brs), 7.51 (1H, m), 7.66 (1H, s). IR (KBr) cm$^{-1}$: 3437, 1655, 1608, 1510, 1497, 1438, 1240. Mass m/z: 434(M$^+$).

Example 8

Production of 2-(4-chlorobenzyl)-6-(2,3-dihydro-1-benzofuran-5-yl)-4-(4-methyl-1-piperazinyl)methyl-2H-pyridazin-3-one 1) Production of 4-carboxy-2-(4-chlorobenzyl)-6-(2,3-dihydro-1-benzofuran-5-yl)-2H-pyridazin-3-one The general procedure of Example 1 (3) was carried out by use of 6-(2,3-dihydro-1-benzofuran-5-yl)-4-methoxycarbonyl-2H-pyridazin-3-one and 4-chlorobenzyl chloride, to thereby yield the title compound as a yellow powder (yield: 89.3%).

m.p.: 200-210° C. ¹H NMR (400 MHz, CDCl$_3$)δ: 3.30 (2H, t, J=8.8 Hz), 4.68 (2H, t, J=8.8 Hz), 5.45 (2H, s), 6.89 (1H, d, J=8.5 Hz), 7.35 (2H, d, J=8.5 Hz), 7.46 (2H, d, J=8.5 Hz), 7.62 (1H, dd, J=8.5, 2.0 Hz), 7.70 (1H, d, J=2.0 Hz), 8.61 (1H, s), 14.02 (1H, brs).

2) Production of 2-(4-chlorobenzyl)-6-(2,3-dihydro-1-benzofuran-5-yl)-4-hydroxymethyl-2H-pyridazin-3-one The general procedure of Example 1 (4) was repeated by use of 4-carboxy-2-(4-chlorobenzyl)-6-(2,3-dihydro-1-benzofuran-5-yl)-2H-pyridazin-3-one, to thereby yield the title compound as a pale yellow powder (yield: 32.7%).

m.p.: 129-134° C. ¹H NMR (400 MHz, CDCl$_3$)δ: 3.28 (2H, t, J=8.8 Hz), 4.64 (2H, t, J=8.8 Hz), 4.69 (2H, s), 5.35 (2H, s), 6.85 (1H, d, J=8.3 Hz), 7.28-7.32 (2H, m), 7.41-7.43 (2H, m), 7.55 (1H, m), 7.65 (1H, m), 7.66 (1H, brs).

3) Production of 2-(4-chlorobenzyl)-6-(2,3-dihydro-1-benzofuran-5-yl)-4-methanesulfonyloxymethyl-2H-pyridazin-3-one The general procedure of Example 1 (5) was carried out by use of 2-(4-chlorobenzyl)-6-(2,3-dihydro-1-benzofuran-5-yl)-4-hydroxymethyl-2H-pyridazin-3-one, to thereby yield the title compound as a yellow powder (yield: 96.6%).

m.p.: 69-70° C. ¹H NMR (400 MHz, CDCl$_3$)δ: 3.15 (3H, s), 3.29 (2H, t, J=8.8 Hz), 4.65 (2H, t, J=8.8 Hz), 5.24 (2H, s), 5.34 (2H, s), 6.86 (1H, d, J=8.3 Hz), 7.30-7.32 (2H, m), 7.41-7.43 (2H, m), 7.55 (1H, m), 7.65 (1H, m), 7.75 (1H, m).

4) Production of 2-(4-chlorobenzyl)-6-(2,3-dihydro-1-benzofuran-5-yl)-4-(4-methyl-1-piperazinyl)methyl-2H-pyridazin-3-one The general procedure of Example 1 (6) was carried out by use of 2-(4-chlorobenzyl)-6-(2,3-dihydro-1-benzofuran-5-yl)-4-methanesulfonyloxymethyl-2H-pyridazin-3-one, to thereby yield the title compound as faint yellow needle-like crystal (yield: 46.3%).

m.p.: 149-150° C. ¹H NMR (400 MHz, CDCl$_3$)δ: 2.55 (3H, s), 2.75-2.95 (8H, m), 3.29 (2H, t, J=8.5 Hz), 3.61 (2H, s), 4.65 (2H, t, J=8.5 Hz), 5.33 (2H, s), 6.86 (1H, d, J=8.3 Hz), 7.29 (2H, d, J=8.3 Hz), 7.43 (2H, d, J=8.3 Hz), 7.53 (1H, brs, J=8.3 Hz), 7.64-7.70 (2H, m). IR (KBr) cm$^{-1}$: 1654, 1609, 1499, 1241, 1118, 808. Mass m/z: 450(M$^+$), 452(M$^+$).

Example 9

Production of 2-(4-chlorocinnamyl)-6-(2,3-dihydro-1-benzofuran-5-yl)-4-(4-methyl-1-piperazinyl)methyl-2H-pyridazin-3-one 1) Production of 4-carboxy-2-(4-chlorocinnamyl)-6-(2,3-dihydro-1-benzofuran-5-yl)-2H-pyridazin-3-one The general procedure of Example 1 (3) was carried out by use of 6-(2,3-dihydro-1-benzofuran-5-yl)-4-methoxycarbonyl-2H-pyridazin-3-one and 4-chlorocinnamyl chloride, to thereby yield the title compound as an orange powder (yield: 44.4%).

m.p.: 177-181° C. ¹H NMR (400 MHZ, CDCl$_3$)δ: 3.29 (2H, t, J=8.5 Hz), 4.67 (2H, t, J=8.5 Hz), 5.09 (2H, dd, J=6.7, 1.2 Hz), 6.39 (1H, dt, J=15.9, 6.7 Hz), 6.73 (1H, d, J=15.9 Hz), 6.89 (1H, d, J=8.5 Hz), 7.29 (2H, d, J=8.5 Hz), 7.33 (2H, d, J=8.5 Hz), 7.64 (1H, dd, J=8.5, 2.0 Hz), 7.70 (1H, d, J=2.0 Hz), 8.63 (1H, s).

2) Production of 2-(4-chlorocinnamyl)-6-(2,3-dihydro-1-benzofuran-5-yl)-4-hydroxymethyl-2H-pyridazin-3-one The general procedure of Example 1 (4) was carried out by use of 4-carboxy-2-(4-chlorocinnamyl)-6-(2,3-dihydro-1-benzofuran-5-yl)-2H-pyridazin-3-one, to thereby yield the title compound as a pale yellow powder (yield: 31.1%).

m.p.: 131-141° C. ¹H NMR (400 MHz, CDCl$_3$)δ: 3.27 (2H, t, J=8.5 Hz), 4.64 (2H, t, J=8.5 Hz), 4.71 (2H, d, J=1.2 Hz), 4.98 (2H, dd, J=6.6, 1.2 Hz), 6.41 (1H, dt, J=15.9, 6.6 Hz), 6.65 (1H, d, J=15.9 Hz), 6.85 (1H, d, J=8.3 Hz), 7.26 (2H, d, J=8.8 Hz), 7.31 (2H, d, J=8.8 Hz), 7.56 (1H, brs, J=8.8 Hz), 7.66 (1H, brs), 7.68 (1H, brs).

3) Production of 2-(4-chlorocinnamyl)-6-(2,3-dihydro-1-benzofuran-5-yl)-4-methanesulfonyloxymethyl-2H-pyridazin-3-one The general procedure of Example 1 (5) was repeated by use of 2-(4-chlorocinnamyl)-6-(2,3-dihydro-1-benzofuran-5-yl)-4-hydroxymethyl-2H-pyridazin-3-one, to thereby yield the title compound as a pale yellow powder (yield: 83.3%).

m.p.: 135-140° C. ¹H NMR (400 MHz, CDCl$_3$)δ: 3.16 (3H, s), 3.28 (2H, t, J=8.5 Hz), 4.65 (2H, t, J=8.5 Hz), 4.98 (2H, dd, J=6.6, 1.2 Hz), 5.28 (2H, d, J=1.2 Hz), 6.39 (1H, dt, J=15.9, 6.6 Hz), 6.66 (1H, d, J=15.9 Hz), 6.86 (1H, d, J=8.5 Hz), 7.27 (2H, d, J=8.5 Hz), 7.31 (2H, d, J=8.5 Hz), 7.57 (1H, brs, J=8.5 Hz), 7.67 (1H, brs), 7.77 (1H, t, J=1.2 Hz).

4) Production of 2-(4-chlorocinnamyl)-6-(2,3-dihydro-1-benzofuran-5-yl)-4-(4-methyl-1-piperazinyl)methyl-2H-pyridazin-3-one The general procedure of Example 1 (6) was carried out by use of 2-(4-chlorocinnamyl)-6-(2,3-dihydro-1-benzofuran-5-yl)-4-methanesulfonyloxymethyl-2H-pyridazin-3-one, to thereby yield the title compound as a faint brown powder (yield: 45.8%).

m.p.: 112-113° C. ¹H NMR (400 MHz, CDCl$_3$)δ: 2.49 (3H, s), 2.60-2.84 (8H, m), 3.29 (2H, t, J=8.5 Hz), 3.61 (2H, brs), 4.64 (2H, t, J=8.5 Hz), 4.97 (2H, d, J=6.3 Hz), 6.42 (1H, dt, J=15.9, 6.3 Hz), 6.66 (1H, d, J=15.9 Hz), 6.86 (1H, d, J=8.3 Hz), 7.25 (2H, d, J=8.5 Hz), 7.31 (2H, d, J=8.5 Hz), 7.54 (1H, d, J=8.3 Hz), 7.69 (1H, s), 7.72 (1H, s). IR (KBr) cm$^{-1}$: 1648, 1607, 1496, 1238, 1091, 807. Mass m/z: 476 (M$^+$), 478(M$^+$).

Example 10

Production of 2-(4-chlorocinnamyl)-6-(2,3-dihydro-1-benzofuran-5-yl)-4-(4-methyl-1-piperazinyl)methyl-2H-pyridazin-3-one dihydrochloride The general procedure of Example 7 was repeated by use of 2-(4-chlorocinnamyl)-6-(2,3-dihydro-1-benzofuran-5-yl)-4-(4-methyl-1-piperazinyl)methyl-2H-pyridazin-3-one, to thereby yield the title compound as a pale brown crystalline powder (yield: 40.5%).

m.p.: 248-251° C. ¹H NMR (400 MHz, DMSO-d$_6$)δ: 2.81 (3H, s), 3.25 (2H, t, J=8.8 Hz), 3.50-4.00 (10H, m), 4.60 (2H, t, J=8.8 Hz), 4.97 (2H, d, J=5.6 Hz), 6.42 (1H, dt, J=16.3, 5.6 Hz), 6.64 (1H, d, J=16.3 Hz), 6.89 (1H, d, J=8.3 Hz), 7.37 (2H, d, J=8.5 Hz), 7.47 (1H, m), 7.49 (2H, d, J=8.5 Hz), 766 (1H, dd, J=8.3, 2.0 Hz), 7.79 (1H, s). IR (KBr) cm$^{-1}$: 1652, 1607, 1492, 1239, 1091, 933.

Example 11

Production of 6-(1-benzofuran-5-yl)-2-(4-fluorobenzyl)-4-(4-methyl-1-piperazinyl)methyl-2H-pyridazin-3-one 1) Production of 5-acetyl-1-benzofuran 5-Acetyl-2-methoxycarbonyl-1-benzofuran [Ramachandra P. K., Cheng T., Horton W. T., *J. Org. Chem.* 28 2744 (1963)] (795 mg, 3.64 mmol) was dissolved in methanol (7 mL), and 20% sodium hydroxide (7 mL) was added to the solution. The mixture was stirred for one hour at 60° C., followed by concentrating under reduced pressure. Subsequently, the reaction mixture was acidified with hydrochloric acid. The formed precipitates were collected through filtration, washed with water and dried, to thereby yield 667 mg of a carboxylic acid product. The product was heated with quinoline (3.3 g) and copper powder (133 mg) at 200° C. for six hours in a nitrogen atmosphere. After cooling, the mixture was dissolved in ethyl acetate, followed by washing sequentially with diluted hydrochloric acid, saturated aqueous sodium bicarbonate, and saturated brine. The mixture was dried over sodium sulfate anhydrate, and the solvent was removed through distillation, to thereby yield 517 mg of the title compound as a blackish brown powder (88.7%).

$^1$H NMR (400 MHz, CDCl$_3$)δ: 2.67 (3H, s), 6.87 (1H, dd, J=2.0, 1.0 Hz), 7.55 (1H, d, J=8.8 Hz), 7.70 (1H, d, J=2,4 Hz), 7.98 (1H, dd, J=8.8, 2.0 Hz), 8.26 (1H, d, J=2.4 Hz). Mass m/z: 160(M$^+$).

2) Production of 6-(1-benzofuran-5-yl)-4-carboxy-2H-pyridazin-3-one

5-Acetyl-1-benzofuran (536 mg, 3.35 mmol) and diethyl ketomalonate (642 mg, 3.69 mmol) were mixed together, and the mixture was stirred for 34 hours at 120° C. Hydrazine monohydrate (247 mg, 4.93 mmol) was added to a solution of the reaction mixture in isopropanol (8.5 mL), and the resultant mixture was heated with stirring for six hours at 100° C. A 2-mol/L aqueous sodium hydroxide solution (5.2 mL) was added thereto, and the mixture was further stirred for four hours at 100° C. The mixture was cooled with ice, and concentrated hydrochloric acid was added thereto, to thereby acidify the heated system. The formed precipitates were collected through filtration, thoroughly washed with water, and dried, to thereby yield 397 mg of the title compound as a yellow powder (46.2%).

3) Production of 6-(1-benzofuran-5-yl)-4-methoxycarbonyl-2H-pyridazin-3-one

The general procedure of Example 1 (3) was carried out by use of 6-(1-benzofuran-5-yl)-4-carboxy-2H-pyridazin-3-one, to thereby yield the title compound as a pale yellow powder (yield: 95.6%).

m.p.: 222-225° C. $^1$H NMR (400 MHz, CDCl$_3$)δ: 4.01 (3H, s), 6.85 (1H, dd, J=2.0, 0.98 Hz), 7.60 (1H, d, J=8.5 Hz), 7.70 (1H, d, J=2.2 Hz), 7.77 (1H, dd, J=8.5, 2.0 Hz), 8.04 (1H, d, J=2.2 Hz), 8.42 (1H, s).

4) Production of 6-(1-benzofuran-5-yl)-4-carboxy-2-(4-fluorobenzyl)-2H-pyridazin-3-one The general procedure of Example 1 (3) was carried out by use of 6-(1-benzofuran-5-yl)-4-methoxycarbonyl-2H-pyridazin-3-one and 4-fluorobenzyl chloride, to thereby yield the title compound as a yellow powder (yield: 73.4%).

m.p.: 207-210° C. $^1$H NMR (400 MHz, CDCl$_3$)δ: 5.50 (2H, s), 6.88 (1H, dd, J=2.0, 0.98 Hz), 7.05-7.09 (2H, m), 7.53-7.56 (2H, m), 7.63 (1H, d, J=8.8 Hz), 7.72 (1H, d, J=2.2 Hz), 7.82 (1H, dd, J=8.8, 2.0 Hz), 8.08 (1H, d, J=2.2 Hz), 8.72 (1H, s).

5) Production of 6-(1-benzofuran-5-yl)-2-(4-fluorobenzyl)-4-hydroxymethyl-2H-pyridazin-3-one The general procedure of Example 1 (4) was carried out by use of 6-(1-benzofuran-5-yl)-4-carboxy-2-(4-fluorobenzyl)-2H-pyridazin-3-one, to thereby yield the title compound as faint yellow powder (yield: 30.4%).

m.p.: 158-160° C. $^1$H NMR (400 MHz, CDCl$_3$)δ: 4.72 (2H, d, J=1.2 Hz), 5.39 (2H, s), 6.85 (1H, dd, J=2.2, 0.98 Hz), 6.99-7.06 (2H, m), 7.49-7.53 (2H, m), 7.59 (1H, d, J=8.5 Hz), 7.69 (1H, d, J=2.2 Hz), 7.76-7.79 (2H, m), 8.02 (1H, d, J=2.2 Hz).

6) Production of 6-(1-benzofuran-5-yl)-2-(4-fluorobenzyl)-4-methanesulfonyloxymethyl-2H-pyridazin-3-one The general procedure of Example 1 (5) was carried out by use of 6-(1-benzofuran-5-yl)-2-(4-fluorobenzyl)-4-hydroxymethyl-2H-pyridazin-3-one, to thereby yield the title compound as a yellow powder (yield: 85.2%).

m.p.: 162-165° C. $^1$H NMR (400 MHz, CDCl$_3$)δ: 3.16 (3H, s), 5.28 (2H, d, J=1.5 Hz), 5.39 (2H, s), 6.86 (1H, dd, J=2.2, 0.98 Hz), 7.00-7.06 (2H, m), 7.48-7.52 (2H, m), 7.59 (1H, d, J=8.8 Hz), 7.70 (1H, d, J=2.0 Hz), 7.77 (1H, dd, J=8.8, 2.2 Hz), 7.86 (1H, t, J=1.2 Hz), 8.01 (1H, d, J=2.0 Hz).

7) Production of 6-(1-benzofuran-5-yl)-2-(4-fluorobenzyl)-4-(4-methyl-1-piperazinyl)methyl-2H-pyridazin-3-one The general procedure of Example 1 (6) was carried out by use of 6-(1-benzofuran-5-yl)-2-(4-fluorobenzyl)-4-methanesulfonyloxymethyl-2H-pyridazin-3-one, to thereby yield the title compound as pale yellow needle-like crystal (yield: 61.7%).

m.p.: 128-130° C. $^1$H NMR (400 MHz, CDCl$_3$)δ: 2.36 (3H, s), 2.55-2.70 (8H, m), 3.59 (2H, d, J=1.2 Hz), 5.38 (2H, s), 6.86 (1H, dd, J=2.2, 0.98 Hz), 6.99-7.05 (2H, m), 7.49-7.55 (2H, m), 7.59 (1H, d, J=8.5 Hz), 7.69 (1H, d, J=2.2 Hz), 7.77 (1H, dd, J=8.5, 2.2 Hz), 7.83 (1H, s), 8.02 (1H, d, J=2.2 Hz). IR (KBr) cm$^{-1}$: 1651, 1605, 1511, 1241, 1118, 770. Mass m/z: 432 (M$^+$)

Example 12

Production of 2-[3-(2-chlorophenyl)propyl]-6-(2,3-dihydro-1-benzofuran-5-yl)-4-(4-methyl-1-piperazinyl)methyl-2H-pyridazin-3-one 1) Production of 4-carboxy-2-[3-(2-chlorophenyl)propyl]-6-(2,3-dihydro-1-benzofuran-5-yl)-2H-pyridazin-3-one The general procedure of Example 1 (3) was carried out by use of 6-(2,3-dihydro-1-benzofuran-5-yl)-4-methoxycarbonyl-2H-pyridazin-3-one and 3-(2-chlorophenyl)-1-propanol methanesulfonate, to thereby yield the title compound as a yellow powder (yield: 76.8%).

m.p.: 137-140° C. $^1$H NMR (400 MHz, CDCl$_3$)δ: 2.26-2.34 (2H, m), 2.88 (2H, t, J=7.8 Hz), 3.30 (2H, t, J=8.8 Hz), 4.43 (2H, t, J=7.1 Hz), 4.67 (2H, t, J=8.8 Hz), 6.88 (1H, d, J=8.3 Hz), 7.12-7.24 (3H, m), 7.33 (1H, m), 7.63 (1H, dd, J=9.3, 2.0 Hz), 7.71 (1H, brs), 8.59 (1H, s), 14.22 (1H, brs)

2) Production of 2-[3-(2-chlorophenyl)propyl]-6-(2,3-dihydro-1-benzofuran-5-yl)-4-hydroxymethyl-2H-pyridazin-3-one The general procedure of Example 1 (4) was carried out by use of 4-carboxy-2-[3-(2-chlorophenyl)propyl]-6-(2,3- dihydro-1-benzofuran-5-yl)-2H-pyridazin-3-one, to thereby yield the title compound as a yellow oil (yield: 49.6%).

$^1$H NMR (400 MHz, CDCl$_3$)δ: 2.19-2.27 (2H, m), 2.85 (2H, t, J=7.6 Hz), 3.28 (2H, t, J=8.5 Hz), 4.32 (2H, t, J=7.3 Hz), 4.64 (2H, t, J=8.5 Hz), 4.70 (2H, d, J=1.2 Hz), 6.85 (1H, d, J=8.3 Hz), 7.11-7.20 (3H, m), 7.32 (1H, m), 7.55 (1H, dd, J=8.3, 1.2 Hz), 7.63 (1H, s), 7.68 (1H, s).

3) Production of 2-[3-(2-chlorophenyl)propyl]-6-(2,3-dihydro-1-benzofuran-5-yl)-4-methanesulfonyloxymethyl-2H-pyridazin-3-one The general procedure of Example 1 (5) was carried out by use of 2-[3-(2-chlorophenyl)propyl]-6-(2,3-dihydro-1-benzofuran-5-yl)-4-hydroxymethyl-2H-pyridazin-3-one, to thereby yield the title compound as a yellow oil (yield: 9.5.9%).

$^1$H NMR (400 MHz, CDCl$_3$)δ: 2.19-2.27 (2H, m), 2.85 (2H, t, J=7.6 Hz), 3.17 (3H, s), 3.29 (2H, t, J=8.8 Hz), 4.32 (2H, t, J=7.1 Hz), 4.65 (2H, t, J=8.8 Hz), 5.27 (2H, d, J=1.5 Hz), 6.86 (1H, d, J=8.5 Hz), 7.12-7.20 (3H, m), 7.32 (1H, m), 7.56 (1H, dd, J=8.5, 1.2 Hz), 7.67 (1H, s), 7.74 (1H, s).

4) Production of 2-[3-(2-chlorophenyl)propyl]-6-(2,3-dihydro-1-benzofuran-5-yl)-4-(4-methyl-1-piperazinyl)methyl-2H-pyridazin-3-one The general procedure of Example 1 (6) was carried out by use of 2-[3-(2-chlorophenyl)propyl]-6-(2,3-dihydro-1-benzofuran-5-yl)-4-methanesulfonyloxymethyl-2H-pyridazin-3-one, to thereby yield the title compound as a yellow oil (yield: 79.3%).

$^1$H NMR (400 MHz, CDCl$_3$)δ: 2.17-2.26 (2H, m), 2.57 (3H, s), 2.80-2.88 (10H, m), 3.29 (2H, t, J=8.8 Hz), 3.63 (2H, s), 4.31 (2H, t, J=7.3 Hz), 4.65 (2H, t, J=8.8 Hz), 6.86 (1H, d, J=8.5 Hz), 7.11-7.18 (3H, m), 7.28-7.33 (2H, m), 7.52 (1H, s), 7.68 (1H, s). IR (Neat) cm$^{-1}$: 1652, 1608, 1498, 1237, 1015, 753. Mass m/z: 478 (M$^+$), 480 (M$^+$).

Example 13

Production of 2-[3-(2-chlorophenyl)propyl]-6-(2,3-dihydro-1-benzofuran-5-yl)-4-(4-methyl-1-piperazinyl)methyl-2H-pyridazin-3-one dihydrochloride The general procedure of Example 7 was carried out by use of 2-[3-(2-chlorophenyl)propyl]-6-(2,3-dihydro-1-benzofuran-5-yl)-4-(4-methyl-1-piperazinyl)methyl-2H-pyridazin-3-one, to thereby yield the title compound as a pale brown crystalline powder (yield: 77.2%).

m.p.: 228-231° C. $^1$H NMR (400 MHz, DMSO-d$_6$)δ: 2.05-2.15 (2H, m), 2.75-2.85 (2H, m), 2.81 (3H, s), 3.26 (2H, t, J=8.8 Hz), 3.60-4.20 (10H, m), 4.21 (2H, t, J=7.1 Hz), 4.61 (2H, t, J=8.8 Hz), 6.89 (1H, d, J=8.5 Hz), 7.20-7.30 (3H, m), 7.38-7.41 (2H, m), 7.65 (1H, dd, J=8.5, 2.0 Hz), 7.78 (1H, s) IR (KBr) cm$^{-1}$: 1660, 1610, 1499, 1238, 1018, 941.

Example 14

Production of 4-aminomethyl-2-[3-(2-chlorophenyl)propyl]-6-(2,3-dihydro-1-benzofuran-5-yl)-2H-pyridazin-3-one The general procedure of Example 5 was carried out by use of 2-[3-(2-chlorophenyl)propyl]-6-(2,3-dihydro-1-benzofuran-5-yl)-4-methanesulfonyloxymethyl-2H-pyridazin-3-one, to thereby yield the title compound as a yellow oil (yield: 58.3%).

$^1$H NMR (400 MHz, CDCl$_3$)δ: 2.11-2.26 (2H, m), 2.85 (2H, t, J=7.3 Hz), 3.27 (2H, t, J=8.8 Hz), 3.90 (2H, s), 4.31 (2H, t, J=7.3 Hz), 4.63 (2H, t, J=8.8 Hz), 6.84 (1H, d, J=8.5 Hz), 7.10-7.19 (3H, m), 7.32 (1H, m), 7.56 (1H,dd, J=8.5, 2.0 Hz), 7.68 (1H, s), 7.69 (1H, s). IR (Neat) cm$^{-1}$: 1652, 1606, 1498, 1238, 1108, 754. Mass m/z: 395(M$^+$), 397(M$^+$).

Example 15

Production of 2-[3-(4-chlorophenyl)propyl]-6-(2,3-dihydro-1-benzofuran-5-yl)-4-(4-methyl-1-piperazinyl)methyl-2H-pyridazin-3-one 1) Production of 4-carboxy-2-[3-(4-chlorophenyl)propyl]-6-(2,3-dihydro-1-benzofuran-5-yl)-2H-pyridazin-3-one The general procedure of Example 1 (3) was carried out by use of 6-(2,3-dihydro-1-benzofuran-5-yl)-4-methoxycarbonyl-2H-pyridazin-3-one and 3-(4-chlorophenyl)-1-propanol methanesulfonate, to thereby yield the title compound as a yellow powder (yield: 71.0%).

m.p.: 157-160° C. $^1$H NMR (400 MHz, CDCl$_3$)δ: 2.21-2.30 (2H, m), 2.73 (2H, t, J=7.6 Hz), 3.03 (2H, t, J=8.8 Hz), 4.38 (2H, t, J=7.3 Hz), 4.68 (2H, t, J=8.8 Hz), 6.89 (1H, d, J=8.3 Hz), 7.13 (2H, d, J=8.3 Hz), 7.24 (2H, d, J=8.3 Hz), 7.62 (1H, dd, J=8.3, 2.0 Hz), 7.69 (1H, s), 8.58 (1H, s), 14.19 (1H, brs).

2) Production of 2-[3-(4-chlorophenyl)propyl]-6-(2,3-dihydro-1-benzofuran-5-yl)-4-hydroxymethyl-2H-pyridazin-3-one The general procedure of Example 1 (4) was carried out by use of 4-carboxy-2-[3-(4-chlorophenyl)propyl]-6-(2,3-dihydro-1-benzofuran-5-yl)-2H-pyridazin-3-one, to thereby yield the title compound as a yellow oil (yield: 53.3%).

$^1$H NMR (400 MHz, CDCl$_3$)δ: 2.16-2.24 (2H, m), 2.70 (2H, t, J=7.3 Hz), 3.28 (2H, t, J=8.8 Hz), 4.27 (2H, t, J=7.3 Hz), 4.65 (2H, t, J=8.8 Hz), 4.76 (2H, d, J=1.2 Hz), 6.85 (1H, d, J=8.5 Hz), 7.14 (2H, d, J=8.3 Hz), 7.23 (2H, d, J=8.3 Hz), 7.55 (1H, dd, J=8.3, 2.2 Hz), 7.61 (1H, s), 7.66 (1H, brs).

3) Production of 2-[3-(4-chlorophenyl)propyl]-6-(2,3-dihydro-1-benzofuran-5-yl)-4-methanesulfonyloxymethyl-2H-pyridazin-3-one The general procedure of Example 1 (5) was repeated by use of 2-[3-(4-chlorophenyl)propyl]-6-(2,3-dihydro-1-benzofuran-5-yl)-4-hydroxymethyl-2H-pyridazin-3-one, to thereby yield the title compound as a yellow oil (yield: 96.9%).

$^1$H NMR (400 MHz, CDCl$_3$)δ: 2.16-2.23 (2H, m), 2.70 (2H, t, J=7.6 Hz), 3.17 (3H, s), 3.29 (2H, t, J=8.8 Hz), 4.27 (2H, t, J=7.3 Hz), 4.65 (2H, t, J=8.8 Hz), 5.25 (2H, d, J=1.5 Hz), 6.86 (1H, d, J=8.3 Hz), 7.14 (2H, d, J=8.3 Hz), 7.23 (2H, d, J=8.3 Hz), 7.55 (1H, dd, J=8.3, 2.2 Hz), 7.64 (1H, s), 7.73 (1H, s).

4) Production of 2-[3-(4-chlorophenyl)propyl]-6-(2,3-dihydro-1-benzofuran-5-yl)-4-(4-methyl-1-piperazinyl)methyl-2H-pyridazin-3-one The general procedure of Example 1 (6) was repeated by use of 2-[3-(4-chlorophenyl)propyl]-6-(2,3-dihydro-1-benzofuran-5-yl)-4-methanesulfonyloxymethyl-2H-pyridazin-3-one, to thereby yield the title compound as a yellow oil (yield: 62.7%).

$^1$H NMR (400 MHz, CDCl$_3$)δ: 2.15-2.33 (2H, m), 2.37 (3H, s), 2.52-2.72 (10H, m), 3.29 (2H, t, J=8.8 Hz), 3.56 (2H, d, J=1.2 Hz), 4.26 (2H, t, J=7.6 Hz), 4.65 (2H, t, J=8.8 Hz), 6.87 (1H, d, J=8.5 Hz), 7.14 (2H, d, J=8.5 Hz), 7.22 (2H, d, J=8.5 Hz), 7.53 (1H, dd, J=8.5, 2.0 Hz), 7.67 (1H, d,

J=2.0 Hz), 7.69 (1H, s). IR (Neat) cm$^{-1}$: 1649, 1607, 1496, 1237, 1015, 755. Mass m/z: 478 (M$^+$), 480 (M$^+$)

Example 16

Production of 4-aminomethyl-2-[3-(4-chlorophenyl)propyl]-6-(2,3-dihydro-1-benzofuran-5-yl)-2H-pyridazin-3-one The general procedure of Example 5 was repeated by use of 2-[3-(4-chlorophenyl)propyl]-6-(2,3-dihydro-1-benzofuran-5-yl)-4-methanesulfonyloxymethyl-2H-pyridazin-3-one, to thereby yield the title compound as a yellow oil (yield: 54.5%).

$^1$H NMR (400 MHz, CDCl$_3$)δ: 2.15-2.23 (2H, m), 2.70 (2H, t, J=7.3 Hz), 3.27 (2H, t, J=8.8 Hz), 3.90 (2H, s), 4.26 (2H, t, J=7.3 Hz), 4.64 (2H, t, J=8.8 Hz), 6.84 (1H, d, J=8.5 Hz), 7.14 (2H, d, J=8.5 Hz), 7.22 (2H, d, J=8.5 Hz), 7.55 (1H, dd, J=8.5, 2.0 Hz), 7.65-7.67 (2H, m). IR (Neat) cm$^{-1}$: 1652, 1606, 1496, 1238, 1103, 756. Mass m/z: 395 (M$^+$) 397 (M$^+$)

Example 17

Production of 2-(2-chlorobenzyl)-6-(2,3-dihydro-1-benzofuran-5-yl)-4-(4-methyl-1-piperazinyl)methyl-2H-pyridazin-3-one 1) Production of 4-carboxy-2-(2-chlorobenzyl)-6-(2,3-dihydro-1-benzofuran-5-yl)-2H-pyridazin-3-one The general procedure of Example 1 (3) was carried out by use of 6-(2,3-dihydro-1-benzofuran-5-yl)-4-methoxycarbonyl-2H-pyridazin-3-one and 2-chlorobenzyl chloride, to thereby yield the title compound as yellow needle-like crystal (yield: 75.0%).

m.p.: 177.9-178.6° C. $^1$H NMR (400 MHz, CDCl$_3$)δ: 3.27 (2H, t, J=8.5 Hz), 4.65 (2H, t, J=8.5 Hz), 5.66 (2H, s), 6.85 (1H, d, J=8.5 Hz), 7.23-7.33 (3H, m), 7.45 (1H, m), 7.59 (1H, dd, J=8.5, 2.0 Hz), 7.67 (1H, d, J=1.5 Hz), 8.65 (1H, s), 14.03 (1H, s). IRKBr cm$^{-1}$: 1756, 1638, 1577, 1499, 1476, 1456, 1435, 1303, 1244.

2) Production of 2-(2-chlorobenzyl)-6-(2,3-dihydro-1-benzofuran-5-yl)-4-hydroxymethyl-2H-pyridazin-3-one The general procedure of Example 1 (4) was repeated by use of 4-carboxy-2-(2-chlorobenzyl)-6-(2,3-dihydro-1-benzofuran-5-yl)-2H-pyridazin-3-one, to thereby yield the title compound as pale yellow needle-like crystal (yield: 42.8%).

m.p.: 158.3-159.0° C. $^1$H NMR (400 MHz, CDCl$_3$)δ: 3.23 (2H, t, J=8.8 Hz), 4.41 (2H, t, J=8.8 Hz), 4.71 (2H, d, J=1.2 Hz), 5.53 (2H, s), 6.81 (1H, d, J=8.5 Hz), 7.13-7.24 (3H, m), 7.40 (1H, m), 7.53 (1H, dd, J=8.5, 2.0 Hz), 7.65 (1H, d, J=1.5 Hz), 7.72 (1H, t, J=1.2 Hz). IR (KBr) cm$^{-1}$: 3402, 1656, 1614, 1596, 1498, 1442, 1235. Mass m/z: 368 (M$^+$), 370 (M$^+$)

3) Production of 2-(2-chlorobenzyl)-6-(2,3-dihydro-1-benzofuran-5-yl)-4-methanesulfonyloxymethyl-2H-pyridazin-3-one The general procedure of Example 1 (5) was repeated by use of 2-(2-chlorobenzyl)-6-(2,3-dihydro-1-benzofuran-5-yl)-4-hydroxymethyl-2H-pyridazin-3-one, to thereby yield the title compound as pale yellow needles (yield: 74.7%).

m.p.: 118.2-118.9° C. $^1$H NMR (400 MHz, CDCl$_3$)δ: 3.16 (3H, s), 3.25 (2H, t, J=8.8 Hz), 4.63 (2H, t, J=8.8 Hz), 5.28 (2H, d, J=1.5 Hz), 5.54 (2H, s), 6.83 (1H, d, J=8.3 Hz), 7.16-7.27 (3H, m), 7.41 (1H, m), 7.53 (1H, dd, J=8.3, 2.0 Hz), 7.64 (1H, d, J=1.5 Hz), 7.80 (1H, t, J=1.2 Hz). IR (KBr) cm$^{-1}$: 1655, 1608, 1398, 1444, 1356, 1242, 1166, 1040. Mass m/z: 446 (M$^+$), 448 (M$^+$)

4) Production of 2-(2-chlorobenzyl)-6-(2,3-dihydro-1-benzofuran-5-yl)-4-(4-methyl-1-piperazinyl)methyl-2H-pyridazin-3-one The general procedure of Example 1 (6) was repeated by use of 2-(2-chlorobenzyl)-6-(2,3-dihydro-1-benzofuran-5-yl)-4-methanesulfonyloxymethyl-2H-pyridazin-3-one, to thereby yield the title compound as pale yellow needle-like crystal (yield: 42.5%).

m.p.: 141.4-142.1° C. $^1$H NMR (400 MHz, CDCl$_3$)δ: 2.35 (3H, s), 2.64 (4H, brs), 2.78 (4H, brs), 3.26 (2H, t, J=8.8 Hz), 3.60 (2H, d, J=1.5 Hz), 4.63 (2H, t, J=8.8 Hz), 5.54 (2H, s), 6.88 (1H, d, J=8.3 Hz), 7.14-7.24 (3H, m), 7.40 (1H, m), 7.53 (1H, dd, J=8.3, 2.0 Hz), 7.66 (1H, s), 7.78 (1H, s). IR (KBr) cm$^{-1}$: 1656, 1611, 1498, 1440, 1323, 1297, 1238. Mass m/z: 450 (M$^+$), 452 (M$^+$)

Example 18

Production of 4-aminomethyl-2-(2-chlorobenzyl)-6-(2,3-dihydro-1-benzofuran-5-yl)-2H-pyridazin-3-one The general procedure of Example 5 was repeated by use of 2-(2-chlorobenzyl)-6-(2,3-dihydro-1-benzofuran-5-yl)-4-methanesulfonyloxymethyl-2H-pyridazin-3-one, to thereby yield the title compound as pale yellow needle-like crystal (yield: 45.8%).

m.p.: 120.1-122.8° C. $^1$H NMR (400 MHz, CDCl$_3$)δ: 3.24 (2H, t, J=8.8 Hz), 3.93 (2H, s), 4.62 (2H, t, J=8.8 Hz), 5.28 (2H, d, J=1.5 Hz), 5.54 (2H, s), 6.82 (1H, d, J=8.5 Hz), 7.14-7.26 (3H, m), 7.39 (1H, m), 7.54 (1H, dd, J=8.3, 2.0 Hz), 7.66 (1H, s), 7.75 (1H, s). IR (KBr) cm$^{-1}$: 3354, 1654, 1613, 1499, 1438, 1239. Mass m/z: 367(M$^+$), 369(M$^+$).

Test Example 1

Method for Determining TNF-α Production Inhibitory Effect

RAW264.7 cells were suspended in a DMEM medium supplemented with 10% fetal bovine serum (FBS), and the suspension was seeded in wells of a 24-well plate (5×10$^5$/mL/well). Each test compound (0 to 10 μM) was added to the wells, and the mixture was incubated in a CO$_2$ incubator for 30 minutes. Subsequently, lipopolysaccharide was added to the mixture in an amount of 1 μg/mL, and incubation was further performed in a CO$_2$ incubator for eight hours. Eight hours after the start of incubation, the culture supernatant was collected, and the amount of TNF-α contained in the culture broth was determined through ELISA. IC$_{50}$ value was determined through comparison with the amount of produced TNF-α in the drug-free (blank) case. The results regarding some representative compounds are shown in Table 1.

TABLE 1

[Structure: pyridazinone core with R¹ substituent on N, CH₂NR²R³ group, and benzofuran-5-yl substituent]

----- : Bond between 2- and 3-positions of benzofuran

| Example No. | (bond) | R¹ | R²(R³)N | TNF-α production inhibitory effect IC50 (μM) |
|---|---|---|---|---|
| 1 | Single bond | ethyl-cyclopropyl | MeN(piperazine)N | 8.9 |
| 6 | Single bond | 4-F-C₆H₄-CH₂ | MeN(piperazine)N | 3.1 |
| 9 | Single bond | 4-Cl-C₆H₄-CH=CH-CH₂- | MeN(piperazine)N | 4.2 |
| 12 | Single bond | 2-Cl-C₆H₄-(CH₂)₃- | MeN(piperazine)N | 2.2 |
| 17 | Single bond | 2-Cl-C₆H₄-CH₂- | MeN(piperazine)N | 7.5 |
| 18 | Single bond | 2-Cl-C₆H₄-CH₂- | NH₂ | 7.5 |

Test Example 2

Test on Absorption after Oral Administration in Mouse

Each of the test compounds (Examples 7, 10, and 13) was suspended in 0.5% HPMC in a mortar. The suspension was orally administered to each male ICR mouse (6 weeks old) in an amount of 10 mg/kg. At each time of 0.25, 0.5, 1, and 4 hours after oral administration, a blood sample was collected and centrifuged, whereby a plasma sample was prepared. The level of the test compound in the plasma sample was determined through HPLC. The results are shown in FIG. 1. As is clear from FIG. 1, the compounds according to the present invention exhibit good absorbability, indicating that the compounds are useful as drugs which can be orally administered.

What is claimed is:

1. A benzofuran derivative represented by formula (1):

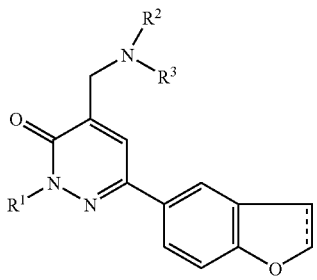

(wherein $R^1$ represents an alkyl group which may have a substituent or an alkenyl group which may have a substituent;
each of $R^2$ and $R^3$ represents a hydrogen atom, an alkyl group, a hydroxyalkyl group, a dihydroxyalkyl group, or an alkynyl group, or $R^2$ and $R^3$ form, together with the nitrogen atom adjacent thereto, a nitrogen-containing saturated heterocyclic group which may have a substituent; and
the broken line denotes the possible presence of a double bond;
wherein the substituent which may be possessed by the alkyl or alkenyl group represented by $R^1$ is a C6-C14 aryl group or a heteroaryl group having a 5-membered or 6-membered ring containing one to three nitrogen atoms, and the aryl or heteroaryl group may be substituted by one to three members selected from the group consisting of halogen atoms, alkyl groups, and alkoxy groups; and
wherein the substituent which may be possessed by the heterocyclic group formed by $R^2$ and $R^3$ is a halogen atom, alkyl group, alkoxycarbonyl group, or aralkyl group)
or a salt thereof.

2. A compound according to claim 1, wherein $R^1$ is a C1-C12 alkyl group which may have a substituent or a C2-C12 alkenyl group which may have a substituent;
wherein the substituent which may be possessed by the alkyl or alkenyl group represented by $R^1$ is a C6-C14 aryl group or a heteroaryl group having a 5-membered or 6-membered ring containing one to three nitrogen atoms, and the aryl or heteroaryl group may be substituted by one to three members selected from the group consisting of halogen atoms, alkyl groups, and alkoxy groups.

3. A compound according to claim 1, wherein each of $R^2$ and $R^3$ represents a hydrogen atom, alkyl group, hydroxyalkyl group, dihydroxyalkyl group, or alkynyl group, or $R^2$ and $R^3$ form, together with the nitrogen atom adjacent thereto, a 5-membered, 6-membered, or 7-membered nitrogen-containing saturated heterocyclic group, and the heterocyclic group may be substituted by a halogen atom, alkyl group, alkoxycarbonyl group, or aralkyl group.

4. A compound according to claim 1, wherein $R^1$ represents a cyclopropylmethyl group, a cinnamyl group, a halogenocinnamyl group, a benzyl group, a halogenobenzyl group, a dihalogenobenzyl group, or a (halogenophenyl) propyl group; each of $R^2$ and $R^3$ is a hydrogen atom, a C1-C7 alkyl group, or a C1-C7 hydroxyalkyl group; or $R^2$ and $R^3$ form together with the nitrogen atom adjacent thereto, a piperazinyl group which may be substituted by a C1-C7 alkyl group.

5. A compound according to claim 1, which is 2-cyclopropylmethyl-6-(2,3-dihydro-1-benzofuran-5-yl)-4-(4-methyl-1-piperazinyl)methyl-2H-pyridazin-3-one, 4-N,N,-bis(2-hydroxyethyl)aminomethyl-2-cyclopropylmethyl-6-(2,3-dihydro-1-benzofuran-5-yl)-2H-pyridazin-3-one, 2-cyclopropylmethyl-6-(2,3-dihydro-1-benzofuran-5-yl)-4-dimethylaminomethyl-2H-pyridazin-3-one, 2-cyclopropylmethyl-6-(2,3-dihydro-1-benzofuran-5-yl)-4-(1-piperazinyl)methyl-2H-pyridazin-3-one, 4-aminomethyl-2-cyclopropylmethyl-6-(2,3-dihydro-1-benzofuran-5-yl)-2H-pyridazin-3-one, 2-(4-fluorobenzyl)-6-(2,3-dihydro-1-benzofuran-5-yl)-4-(4-methyl-1-piperazinyl)methyl-2H-pyridazin-3-one, 2-(4-chlorobenzyl)-6-(2,3-dihydro-1-benzofuran-5-yl)-4-(4-methyl-1-piperazinyl)methyl-2H-pyridazin-3-one, 2-(4-chlorocinnamyl)-6-(2,3-dihydro-1-benzofuran-5-yl)-4-(4-methyl-1-piperazinyl)methyl-2H-pyridazin-3-one, 6-(1-benzofuran-5-yl)-2-(4-fluorobenzyl)-4-(4-methyl-1-piperazinyl)methyl-2H-pyridazin-3-one, 2-[3-(2-chlorophenyl)propyl]-6-(2,3-dihydro-1-benzofuran-5-yl)-4-(4-methyl-1-piperazinyl)methyl-2H-pyridazin-3-one, 4-aminomethyl-2-[3-(2-chlorophenyl)propyl]-6-(2,3-dihydro-1-benzofuran-5-yl)-2H-pyridazin-3-one, 2-[3-(4-chlorophenyl)propyl]-6-(2,3-dihydro-1-benzofuran-5-yl)-4-(4-methyl-1-piperazinyl)methyl-2H-pyridazin-3-one, 4-aminomethyl-2-[3-(4-chlorophenyl)propyl]-6-(2,3-dihydro-1-benzofuran-5-yl)-2H-pyridazin-3-one, 2-(2-chlorobenzyl)-6-(2,3-dihydro-1-benzofuran-5-yl)-4-(4-methyl-1-piperazinyl)methyl-2H-pyridazin-3-one, or 4-aminomethyl-2-(2-chlorobenzyl)-6-(2,3-dihydro-1-benzofuran-5-yl)-2H-pyridazin-3-one.

6. A pharmaceutical composition containing a compound or a salt thereof as recited in claim 1, and a pharmacologically acceptable carrier therefor.

7. A method for treating a patient with a disease or condition in which excessive production of tumor necrosis factor (TNF-α) is implicated, comprising administering a compound or a salt thereof as recited in claim 1 to said patient, wherein said disease or condition is rheumatism, arthritis, or ulcerative colitis.

8. A compound according to claim 2, wherein each of $R^2$ and $R^3$ represents a hydrogen atom, alkyl group, hydroxyalkyl group, dihydroxyalkyl group, or alkynyl group, or $R^2$ and $R^3$ form, together with the nitrogen atom adjacent thereto, a 5-membered, 6-membered, or 7-membered nitrogen-containing saturated heterocyclic group, and the heterocyclic group may be substituted by a halogen atom, alkyl group, alkoxycarbonyl group, or aralkyl group.

9. A process for preparing the benzofuran derivative according to claim 1, comprising carrying out the following reaction scheme:

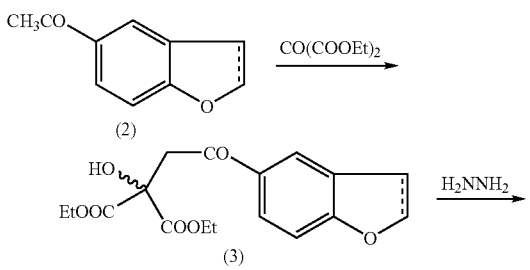

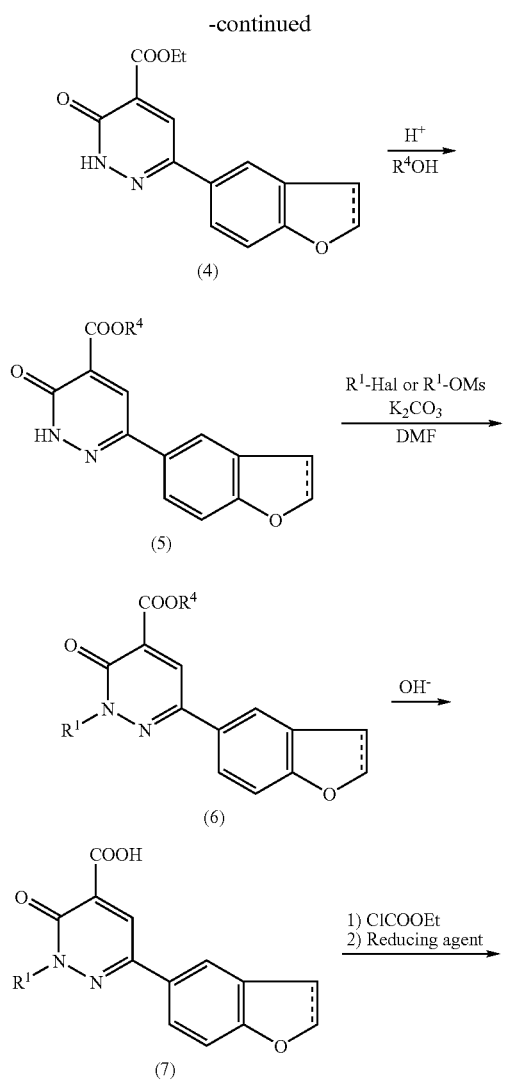
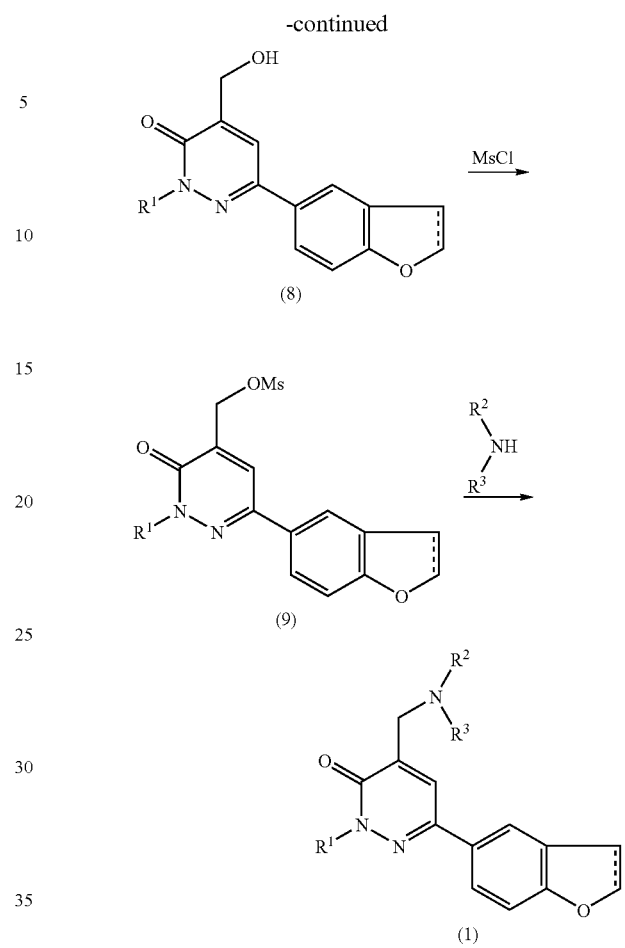
wherein $R^4$ represents an alkyl group; Hal represents a halogen atom; and Ms represents a methanesulfonyl group.
* * * * *